United States Patent [19]

Breuer et al.

[11] Patent Number: 4,461,767
[45] Date of Patent: Jul. 24, 1984

[54] IMINOTHIAZOLYL UREIDO CEPHALOSPORINS

[75] Inventors: Hermann Breuer; Uwe D. Treuner; Theodor Denzel, all of Regensburg, Fed. Rep. of Germany

[73] Assignee: E. R. Squibb & Sons, Inc., Princeton, N.J.

[21] Appl. No.: 46,068

[22] Filed: Jun. 6, 1979

Related U.S. Application Data

[63] Continuation-in-part of Ser. No. 916,380, Jun. 16, 1978, abandoned.

[51] Int. Cl.³ .................. A61K 31/545; C07D 501/56
[52] U.S. Cl. ...................................... 424/246; 544/21; 544/22; 544/25; 544/27; 544/28
[58] Field of Search .................... 544/27, 21; 424/246

[56] References Cited
U.S. PATENT DOCUMENTS

| 4,008,246 | 2/1977 | Ochiai et al. | 544/27 |
| 4,097,595 | 6/1978 | Heymés | 544/27 |
| 4,098,888 | 7/1978 | Ochiai et al. | 424/246 |
| 4,127,716 | 11/1978 | Breuer et al. | |
| 4,152,432 | 5/1979 | Heymés et al. | 424/246 |

Primary Examiner—Paul M. Coughlan, Jr.
Attorney, Agent, or Firm—Lawrence S. Levinson; Stephen B. Davis

[57] ABSTRACT

Cephalosporins of the formula wherein R is hydrogen, sodium, potassium or certain ester groups; $R_1$ is in the α-configuration and is hydrogen or methoxy; $R_2$ is hydrogen, $$-\underset{\parallel}{\overset{O}{C}}-CH_2Cl, \quad -\underset{\parallel}{\overset{O}{C}}-CH_2Br, \quad -\underset{\parallel}{\overset{O}{C}}-CF_3, \quad -\underset{\parallel}{\overset{O}{C}}-O-CH_2CCl_3,$$

$-CH$, or $-C-(\text{phenyl})_3$ ; X is hydrogen, $-O-\overset{O}{\underset{\parallel}{C}}-\text{lower alkyl}$, $-O-\overset{O}{\underset{\parallel}{C}}-NH_2$, $-N(\text{pyridyl})$, $-N(\text{pyridyl})CNH_2$, $-S-\overset{N\text{---}N}{\underset{S}{\parallel}}-R_4$, or $-S-\overset{N\text{---}N}{\underset{\underset{R_5}{N}}{\parallel}}$;

$R_4$ is hydrogen or lower alkyl; $R_5$ is hydrogen, lower alkyl, $$-(CH_2)_n-\overset{O}{\underset{\parallel}{C}}-OR_6, \quad -(CH_2)_n-\overset{O}{\underset{\underset{O}{\parallel}}{S}}-OR_6,$$

or $-(CH_2)_n-N-(\text{lower alkyl})_2$; $R_6$ is hydrogen, sodium, or potassium; n is an integer from 1 to 4; are disclosed. These compounds are useful as anti-bacterial agents.

22 Claims, No Drawings

IMINOTHIAZOLYL UREIDO CEPHALOSPORINS

RELATED APPLICATIONS

This application is a continuation-in-part of Ser. No. 916,380 filed June 16, 1978, now abandoned.

BACKGROUND OF THE INVENTION

Cephalosporins having a ureido substituted acyl sidechain and various groups in the 3-position are disclosed by Erickson in U.S. Pat. Nos. 3,673,183, Welch et al. in 3,708,479, Dolfini in 3,833,568, Breuer in 3,860,591, and Breuer et al. in 3,996,217, 3,996,218, and 4,024,135, and Belgian Pat. No. 833,640.

Various 7α-methoxy cephalosporins having a ureido substituted acyl sidechain and various groups in the 3-position are disclosed by Dolfini in U.S. Pat. Nos. 3,978,051, 3,989,693, 3,989,697, 4,000,134, and 4,061,852.

Ochiai et al. in U.S. Pat. No. 4,098,888 disclose cephalosporins having an iminothiazolyl acetamido acyl sidechain with an amino, hydroxy, or imino group on the α-carbon atom of the acyl sidechain.

Cephalosporins having an iminothiazolyl or substituted iminothiazolyl acetamido acyl sidechain and various groups in the 3-position are disclosed by Numata et al. in German Offenlegungsschrift No. 2,461,478. Similarly, desmethoxy cephalosporins having an alkoxyimino or hydroxyimino substituted iminothiazolyl acetamido acyl sidechain and various groups in the 3-position are disclosed in Belgian Pat. Nos. 850,662; 852,860; 852,427; 853,545; and 856,045.

SUMMARY OF THE INVENTION

This invention is directed to the new cephalosporins of the formula (I)

[chemical structure]

R represents hydrogen, sodium, potassium, t-butyl, benzyl, p-methoxybenzyl, p-nitrobenzyl, diphenylmethyl, 2,2,2-trichloroethyl, trimethylsilyl, —CH$_2$—O—lower alkyl,

[chemical structure: —CH(R$_3$)—O—C(=O)—lower alkyl, or O-phthalidyl]

R$_1$ is in the α-configuration and is hydrogen or methoxy.

R$_2$ represents hydrogen,

[chemical structures: —C(=O)—CH$_2$Cl, —C(=O)—CH$_2$Br, —C(=O)—CF$_3$, —C(=O)—O—CH$_2$CCl$_3$, —CH(=O), or —C(phenyl)$_3$]

R$_3$ represents hydrogen or lower alkyl.
X represents hydrogen,

[chemical structures: —O—C(=O)—lower alkyl, —O—C(=O)—NH$_2$, —N-pyrrolidinyl,]

[chemical structures involving pyridine-CNH$_2$, thiazole, thiadiazole with R$_4$, R$_5$]

R$_4$ represents hydrogen or lower alkyl.
R$_5$ represents hydrogen, lower alkyl, —(CH$_2$)$_n$—C(=O)—OR$_6$, —(CH$_2$)$_n$—S(=O)$_2$—OR$_6$, or —(CH$_2$)$_n$—N—(lower alkyl)$_2$.

R$_6$ represents hydrogen, sodium or potassium.
n represents an integer from 1 to 4.

When X is pyridinium or carbamoyl substituted pyridinium, the compounds can be structurally represented as having the formula (Ia)

[chemical structure]

wherein Z is hydrogen or carbamoyl.

DETAILED DESCRIPTION OF THE INVENTION

The lower alkyl groups referred to throughout this specification include straight or branched chain hydrocarbon groups containing 1 to 4 carbons, e.g., methyl, ethyl, i-propyl, t-butyl, etc.

The compounds of formula I and the intermediates that are described below that include the 2-iminothiazolyl group as part of their structure are, of course, tautomeric and can also be structurally represented as a 2-amino group. Thus, for example, the compounds of formula I can be represented as

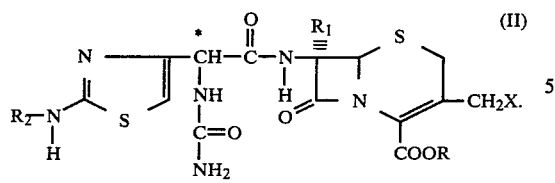

The intermediates and final products are being structurally represented and named throughout this specification as 2-iminothiazoles though both forms are within the scope of the invention.

The compounds of formula I can be prepared by several methods. For example, the compounds of formula I wherein X is hydrogen,

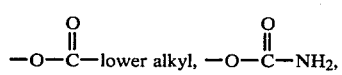

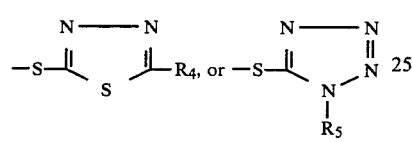

can be prepared by acylating an 7β-amino-7α-methoxy or desmethoxy cephalosporanic acid ester of the formula

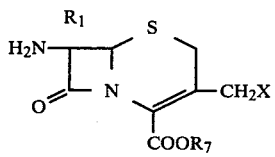

wherein $R_7$ is t-butyl, benzyl, p-methoxybenzyl, p-nitrobenzyl, diphenylmethyl, trimethylsilyl, lower alkoxymethyl, or 2,2,2-trichloroethyl, especially diphenylmethyl, with an activated derivative of the formula

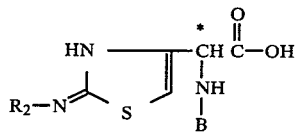

wherein $R_2$ is as defined above and B is a protecting group such as

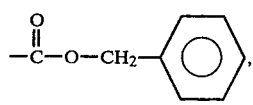

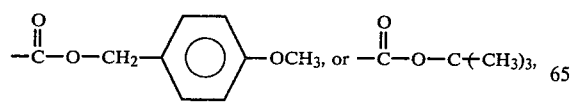

to yield the intermediate of the formula

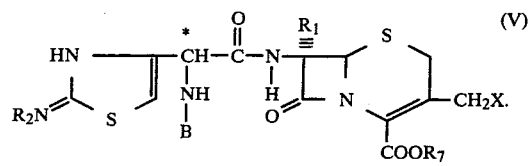

Suitable activated derivatives of the compound of formula IV are the acid chloride or bromide, an anhydride or mixed anhydride, or an activated ester formed according to methods known in the art.

Alternatively, the acylation can be performed directly with the acid compound of formula IV by use of coupling agents such as carbodiimides. This direct acylation process is especially preferred when $R_2$ is hydrogen.

The intermediate of formula V is then treated with trifluoroacetic acid and anisole to yield the α-amino cephalosporin of the formula

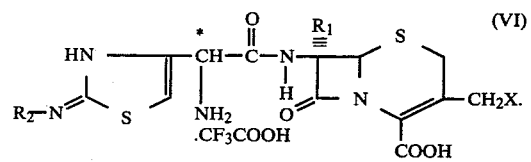

Treatment of the trifluoroacetic acid salt of formula VI with potassium or sodium cyanate yields the compounds of formula I wherein $R_2$ is as defined above.

Alternatively, the 2,3-dihydro-α-protected amino-4-thiazoleacetic acid of formula IV can be treated with trifluoroacetic acid and anisole to yield

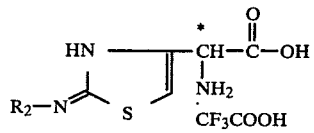

which is treated with potassium cyanate to yield

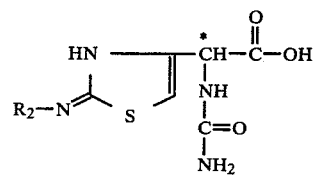

The α-ureido intermediate of formula VIII is then converted to an activated form such as a mixed anhydride or activated ester. Acylation of the ester of formula III with the activated compound of formula VIII yields

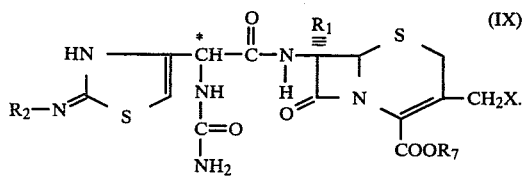

The ester group $R_7$ can then be removed according to known methods to yield the compounds of formula I.

Also, when $R_2$ is

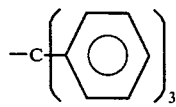

the acid of formula VIII can be treated with thionyl chloride to yield an activated intermediate which can be represented as having the formula

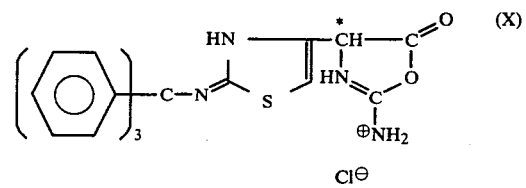
(X)

Acylation of the ester of formula III with the activated compound of formula X yields the compounds of formula I wherein $R_2$ is

The compound of formula IV wherein $R_2$ is hydrogen is prepared by reacting a 2,3-dihydro-2-imino-α-amino-4-thiazoleacetic acid with an amino protecting group such as (p-methoxyphenyl)methoxycarbonylazide. The compounds of formula IV wherein $R_2$ is other than hydrogen are prepared by reacting the compound wherein $R_2$ is hydrogen with the imino protecting group as taught in Belgian Pat. Nos. 850,662; 852,860; 852,427; 853,545; and 856,045 and German Offenlegungsschrift No. 2,461,478 referred to above.

The compounds of formula I wherein $R_2$ is other than hydrogen can be treated according to known procedures to remove the imino protecting group and yield the compounds wherein $R_2$ is hydrogen. For example, the compound of formula I wherein $R_2$ is

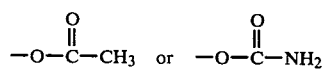

and R is an ester such as diphenylmethyl is first treated with thiourea to remove the

group and is then treated with trifluoroacetic acid and anisole to remove the diphenylmethyl ester group.

The compounds of formula Ia can be prepared by reacting a compound of formula I wherein R is hydrogen and X is

with pyridine or carbamoyl substituted pyridine in a polar solvent such as water and in the presence of a catalyst such as an alkali meta thiocyanate according to the procedures taught in U.S. Pat. No. 3,792,047 and German Offenlegungsschrift No. 2,234,280.

Also, the compounds of formula I wherein X is heterothio

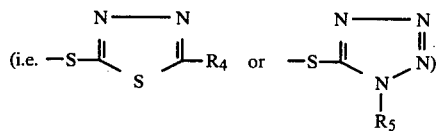

can be prepared by reacting the compound of formula I wherein R is hydrogen and X is

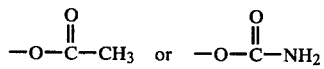

with a mercaptan of the formula hetero—S—H      (XI)

or an alkali metal (preferably sodium) mercaptan salt of the formula hetero—S—alkali metal.      (XII)

Such methods of introducing a heterothio group in the 3-position are disclosed in various U.S. Pat. Nos. including 3,855,213; 4,066,762; etc.

The compounds of formula I wherein R is sodium or potassium are prepared by reacting the corresponding free acid of formula I (R is hydrogen) with the appropriate salt forming ion.

The compounds of formula I wherein R is

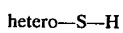

alkyl can be obtained by treating the corresponding free acid of formula I with one or two moles of a compound of the formula

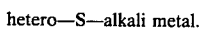
(XIII)

wherein halo is chlorine or bromine in an inert solvent such as dimethylformamide at or below ambient temperature.

Similarly, the compounds of formula I wherein R is

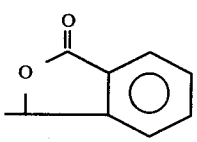

are prepared by treating the free acid compound of formula I with a compound of the formula $$\text{(XIV)} \quad \underset{HO}{\overset{O}{\underset{\|}{\text{C}}}}\text{-benzene ring}$$

as taught by Ferres et al. in U.S. Pat. No. 3,860,579.

The symbol C* in the preceding formulas represents an asymmetric carbon atom.

By selection of the appropriate starting materials, it is possible to obtain the compounds of formula I as a mixture of optically active isomers or isolated as a single isomer. Also, when the final product is obtained in the D,L-form, the pure D- and L-diastereoisomers can be obtained by preparative high performance liquid chromatography (HPLC). The various isomers as well as their mixtures are within the scope of this invention.

Preferred compounds of this invention as final products are those of formula I wherein R is hydrogen, sodium or potassium; $R_1$ is hydrogen; $R_2$ is hydrogen or $$-\overset{O}{\underset{\|}{C}}CH_2Cl$$

especially hydrogen; X is hydrogen, $$-O-\overset{O}{\underset{\|}{C}}-CH_3, \quad -O-\overset{O}{\underset{\|}{C}}-NH_2, \quad -N\bigcirc,$$

$$-N\bigcirc-\overset{O}{\underset{\|}{C}}-NH_2, \quad -S-\underset{S}{\overset{N-N}{\|\!\!\!\!\|}}-CH_3, \text{ or}$$

$$-S-\underset{\underset{R_5}{N}}{\overset{N-N}{\|\!\!\!\!\|}}N;$$

$R_5$ is hydrogen, methyl, $-CH_2-COOR_6$, $$-CH_2-\overset{O}{\underset{\underset{O}{\|}}{S}}-OR_6$$

or $-(CH_2)_2-N(CH_3)_2$; and $R_6$ is hydrogen, sodium or potassium.

Most preferred as final products are the above compounds wherein X is $$-O-\overset{O}{\underset{\|}{C}}-CH_3 \quad \text{or} \quad -S-\underset{\underset{CH_3}{N}}{\overset{N-N}{\|\!\!\!\!\|}}N.$$

Also, preferred as intermediates are the compounds of formula I wherein R is t-butyl, benzyl, diphenylmethyl, or 2,2,2-trichloroethyl; and $R_2$ is $$-\overset{O}{\underset{\|}{C}}-CH_2Cl, \quad -\overset{O}{\underset{\|}{C}}-CH_2Br, \quad -\overset{O}{\underset{\|}{C}}-CF_3, \quad -\overset{O}{\underset{\|}{C}}-O-CH_2CCl_3,$$

$$-\overset{O}{\underset{\|}{C}}H, \quad \text{or} \quad -\overset{O}{\underset{\|}{C}}-(\bigcirc)_3.$$

The compounds of formula I wherein R is hydrogen, sodium, potassium, $-CH_2-O-$lower alkyl, $$-\underset{R_3}{\overset{}{C}}H-O-\overset{O}{\underset{\|}{C}}-\text{lower alkyl, or } O-\overset{O}{\underset{\|}{C}}-\text{benzene}$$

and $R_2$ is hydrogen, $$-\overset{O}{\underset{\|}{C}}-CH_2Cl, \quad -\overset{O}{\underset{\|}{C}}-CH_2Br, \quad -\overset{O}{\underset{\|}{C}}-CF_3,$$

$$-\overset{O}{\underset{\|}{C}}-O-CH_2CCl_3, \text{ or } -\overset{O}{\underset{\|}{C}}H$$

are useful antibacterial agents possessing activity against various gram positive and gram negative organisms such as *Staphylococcus aureus, Escherichia coli, Enterobacter cloacae, Klebsiella pneumoniae, Klebsiella aerogenes, Proteus rettgeri, Proteus vulgarius, Proteus mirabilis, Serratia marcescens, Salmonella typhomurium, Shigella sonnei, Citrobacter freundii,* etc. The preferred and most preferred final products are especially active against the gram negative organisms such as Proteus, *Escherichia coli,* Klebsiella, and Salmonella.

The active final products may be used as antibacterial agents to combat infections due to organisms such as those named above, and in general may be utilized in a manner similar to cephalothin and other cephalosporins. For example, a compound of formula I or a physiologically acceptable salt or ester thereof may be used in various animal species in an amount of about 1 to 100 mg./kg., daily, parenterally, in single or two to four divided doses to treat infections of bacterial origin, e.g., 5.0 mg./kg. in mice.

Up to about 600 mg. of an acid compound of formula I or a physiologically acceptable salt or ester thereof may be incorporated in an injectable form in a sterile aqueous vehicle prepared according to conventional pharmaceutical practice.

Illustrative process details are provided in the Examples for the various reactions. All temperatures are on the centigrade scale.

EXAMPLE 1

7β-[[D,L-[(Aminocarbonyl)amino]-(2-[(chloroacetyl)imino]-2,3-dihydro-4-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid sodium salt (a)

D,L-2,3-Dihydro-2-imino-α-[[[(4-methoxyphenyl)methoxy]carbonyl]amino]-4-thiazoleacetic acid 0.1 mol. of D,L-2,3-Dihydro-2-imino-α-amino-4-thiazoleacetic acid are dissolved in 150 ml. of water and brought into solution by the addition of 0.3 ml. of triethylamine. A solution of 22.7 g. of (p-methoxyphenyl)methoxycarbonylazide in 150 ml. of dioxane is added with vigorous stirring. The turbid mixture becomes clear after 30 minutes. This mixture is then stirred for one hour at room temperature and the dioxane is then distilled off. The aqueous base is extracted with ether, cooled to 0°, and acidified to pH 3.5 by the addition of 2N hydrochloric acid. The desired product crystallizes and is filtered under suction to yield 27 g. of D,L-2,3-dihydro-2-imino-α-[[[(4-methoxyphenyl)methoxy]carbonyl]amino]-4-thiazoleacetic acid; m.p. 141°-142° (dec.).

(b)

D,L-2-[(Chloroacetyl)imino]-2,3-dihydro-α-[[[(4-methoxyphenyl)methoxy]carbonyl]amino]-4-thiazoleacetic acid 34 g. (0.1 mol.) of the product from part (a) are dissolved in 300 ml. of dimethylacetamide and 13.6 g. (0.12 mol.) of chloroacetyl chloride are added dropwise while cooling with ice. The mixture is stirred for one hour at room temperature, cooled, and then extracted several times with ethyl acetate. The combined ethyl acetate extracts are washed with water, dried with magnesium sulfate, treated with activated carbon, and concentrated in vacuo. The residue crystallizes and is triturated with ether and filtered under suction to yield 25.9 g. of D,L-2-[(chloroacetyl)imino]-2,3-dihydro-α-[[[(4-methoxyphenyl)methoxy]carbonyl]amino]-4-thiazoleacetic acid, m.p. 157°-158° (dec.).

(c)

7β-[[D,L-[[[(4-Methoxyphenyl)methoxy]carbonyl]amino]-(2-[(chloroacetyl)imino]-2,3-dihydro-4-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 1.6 g. (0.00386 mol.) of the product from part (c) are dissolved in 30 ml. of anhydrous tetrahydrofuran and combined with a solution of 1.89 g. (0.0032 mol.) of 7β-amino-3-[[(1-methyl-1H-tetrazol-5-yl)thio]methyl]-8-oxo-5-thia-1-azabicyclo[4.2.0]oct-2-ene-2-carboxylic acid, diphenylmethyl ester in 20 ml. of methylene chloride. The mixture is cooled to 0°-5° and a solution of 0.72 g. (0.0035 mol.) of dicyclohexylcarbodiimide in 5 ml. of tetrahydrofuran is added. The mixture is stirred for 90 minutes at 0°-5° and 90 minutes at room temperature. The precipitated dicyclohexylurea is filtered off and the filtrate is evaporated to dryness in vacuo. The residue is added to a mixture of tetrahydrofuran and ethyl acetate and washed with sodium bicarbonate solution. After washing with water, drying with magnesium sulfate, treating with activated carbon and filtering, the mixture is concentrated. The solid residue is triturated with ether and filtered under suction to yield 2.7 g. of 7β-[[D,L-[[[(4-methoxyphenyl)methoxy]carbonyl]amino]-2-[(chloroacetyl)imino]-2,3-dihydro-4-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester, m.p. 165°-167° (dec.).

(d)

7β-[[D,L-(α-Amino-2-[(chloroacetyl)imino]-2,3-dihydro-4-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt 2.6 g. of the diphenylmethyl ester product from part (c) are suspended in 10 ml. of anisole and 20 ml. of trifluoroacetic acid are added dropwise. The clear solution is kept at 0°-5° for 10 minutes and the trifluoroacetic acid is distilled off in vacuo. The residue is treated with ether and filtered under suction to yield 2.1 g. of 7β-[[D,L-(α-amino-2-[(chloroacetyl)imino]-2,3-dihydro-4-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt, m.p. 144°-145° (dec.)

(e)

7β-[D,L-[(Aminocarbonyl)amino]-2-[(chloroacetyl)imino]-2,3-dihydro-4-thiazolyl)acetyl]amino]-3-[[(1-methyl-1H-tetrazol-5-yl)thio]methyl-8-oxo-5-thia-1-azabicyclo[4.2.0]oct-2-ene-2-carboxylic acid, sodium salt 2 g. of the trifluoroacetic acid salt product from part (d) are added to a solution of 0.48 g. of potassium cyanate in 15 ml. of water. The mixture is stirred for three hours at room temperature. The slightly turbid solution is filtered and acidified to a pH of 2.5 while cooling with ice. The resulting precipitate is filtered under suction and dried to obtain 1.2 g. of 7β-[[D,L-[(aminocarbonyl)amino]-(2-[(chloroacetyl)imino]-2,3-dihydro-4-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid, m.p. 230°-231° (dec.).

0.8 g. of the above free acid product are dissolved in a mixture of methanol and acetonitrile (50:50). Slightly more than the molar equivalent proportion of sodium ethylhexanoate are added. The mixture is stirred at room temperature for 20 minutes and ether is added until precipitation is completed to yield 0.6 g. of 7β-[-[D,L-[(aminocarbonyl)amino]-(2-[(chloroacetyl)imino]-2,3-dihydro-4-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid, sodium salt, m.p. 243°-245° (dec.).

EXAMPLE 2

7β-[[D,L-[(Aminocarbonyl)amino]-(2,3-dihydro-2-imino-4-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid, sodium salt (a)

7β-[[D,L-[(Aminocarbonyl)amino]-(2-[(chloroacetyl)imino]-2,3-dihydro-4-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 2 g. of the acid product of Example 1 (e) are dissolved in a mixture of acetonitrile and methanol (1:1). To this is added 4 ml. of a solution of 0.5 mole of diphenyldiazomethane in 200 ml. of dioxane. This mixture is stirred overnight at room temperature and the resulting precipitate is filtered under suction to yield 1.36 g. of 7β-[[D,L-[(aminocarbonyl)amino](2-[(chloroacetyl)imino]-2,3-dihydro-4-thiazolyl)acetyl]amino]-3-[[(1-methyl-1H-tetrazol-5-yl)thio]methyl]-8-oxo-5-thia-1-azobicyclo[4.2.0]oct-2-ene-2-carboxylic acid, diphenylmethyl ester, m.p. 170°-173° (dec.).

Additional diphenylmethyl ester product can be obtained by first adding a small amount of p-toluenesulfonic acid to the filtrate. After the red color of the diphenyldiazomethane disappears, the mixture is concentrated and the residue is triturated with water and ether to yield an additional 1 g. of diphenylmethyl ester product.

(b)

7β-[[D,L-[(Aminocarbonyl)amino]-(2,3-dihydro-2-imino-4-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 1 g. of the diphenylmethyl ester product from part (a) and 0.2 g. of thiourea are refluxed in 50 ml. of a mixture of chloroform, methanol, and dioxane (2:1:1). After refluxing for three hours, the resulting clear solution is concentrated and water is added to the residue to yield 0.9 g. of crude 7β-[[D,L-[(aminocarbonyl)amino](2-,3-dihydro-2-imino-4-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester, m.p. 140°-170° (dec.).

(c)

7β-[[D,L-[(Aminocarbonyl)amino]-(2,3-dihydro-2-imino-4-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid, sodium salt A mixture of 3.44 ml. of trifluoroacetic acid and 1.77 ml. of anisole is added to 0.45 g. of the diphenylmethyl ester product of part (b). After concentrating, the residue is taken up in ether and treated to yield 0.4 g. of 7β-[[D,L-[(aminocarbonyl)amino]-(2,3-dihydro-2-imino-4-thiazolyl)acetyl]amino]-3-[[(1-methyl-1H-tetrazol-5-yl)thio]methyl]-8-oxo-5-thia-1-azabicyclo[4.2.0]oct-2-ene-2carboxylic acid.

The 0.4 g. of free acid product are then suspended in water and brought into solution by the addition of sodium bicarbonate solution. The solution is freeze dried to yield 7β-[[D,L-[(aminocarbonyl)amino]-2(2,3-dihydro-2-imino-4-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid, sodium salt as a white powder. This sodium salt product melts with decomposition at below 225°.

EXAMPLE 3

7β-[[D-[(Aminocarbonyl)amino]-(2,3-dihydro-2-imino-4-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid, sodium salt and 7β-[[L-[(aminocarbonyl)amino]-(2,3-dihydro-2-imino-4-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid, sodium salt The D,L-product obtained from Example 2 is separated into the D- and L-isomers by means of preparative high performance liquid chromatography (HPLC) employing a 7 μm reverse phase C-8 column (25 mm ID×250 mm). The eluant employed is a mixture of methanol and 0.01M phosphate buffer (1:9) at a flow rate of 20 ml/min. The separation is performed at room temperature and the eluant is monitored at 254 nm (UV). The L-isomer separates out first followed by the D-isomer. The separated isomers are then treated by HPLC on a 25–40 μm RP-18 column (16 mm ID×250 mm) employing as the solvent a mixture of methanol and water (1:99).

This procedure yields 7β-[[D-[[(aminocarbonyl)amino]-(2,3-dihydro-2-imino-4-thiazolyl)acetyl]amino]3-[[(1-methyl-1H-tetrazol-5-yl)thio]methyl]-8-oxo-5-thia-1-azabicyclo[4.2.0]oct-2-ene-2-carboxylic acid, sodium salt; NMR ($D_2O$) δ 3.52 (ABq; J=18 Hz, 2H), 4.0 (s,3H), 4.15 (ABq, J=14 Hz, 2H), 5.03 (d, J=5 Hz, 1H), 5.25 (s, 1H), 5.65 (d, J=5 Hz, 1H), and 6.67 (s, 1H); I.R. (KBr) 1760 cm$^{-1}$; UV$_{max}$ 258 nm., ε=12,230; $[α]_D^{24}$ −27.3° (c=4.4 mg./ml; $H_2O$) and 7β-[[L-[[(aminocarbonyl)amino]-(2,3-dihydro-2-imino-4-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid, sodium salt; NMR ($D_2O$) δ 3.60 (ABq; J=18 Hz, 2H), 4.03 (s, 3H), 4.18 (ABq, J=14 Hz, 2H), 5.10 (d, J=5 Hz, 1H), 5.26 (s, 1H), 5.58 (d, J=5 Hz, 1H), and 6.88 (s, 1H);

I.R. (KBr) 1760 cm$^{-1}$; U.V.$_{max}$ 256 nm.; ε=12,470; $[α]_D^{24}$ +43.8° (c=4.2 mg.ml.; $H_2O$).

EXAMPLE 4

7β-[[D,L-[(Aminocarbonyl)amino]-2-[(chloroacetyl)imino]-2,3-dihydro-4-thiazolyl)acetyl]amino]-3-[acetyloxy)methyl]-8-oxo-5-thia-1-azabicyclo[4.2.0]oct-2-ene-2-carboxylic acid, sodium salt (a)

7β-[[D,L-[[[(4-Methoxyphenyl)methoxy]carbonyl]amino]-(2-[(chloroacetyl)imino]-2,3-dihydro-4-thiazolyl)acetyl]amino]-3-[(acetyloxy)methyl]-8-oxo-5-thia-1-azabicyclo[4.2.0]oct-2-ene-2-carboxylic acid, diphenylmethyl ester A solution of 0.033 mol. of dicyclohexylcarbodiimide in tetrahydrofuran is added dropwise at 0°-5° to a solution of 0.036 moles of D,L-2-[(chloroacetyl)imino]-2,3-dihydro-α-[[[(4-methoxyphenyl)methoxy]carbonyl]amino]-4-thiazoleacetic acid from Example 1(b) and 0.03 mol. of 7β-aminocephalosporanic acid, diphenylmethyl ester in tetrahydrofuran. The mixture is stirred for 30 minutes at 0°-5° and one hour at room temperature, then filtered and the filtrate is then concentrated. The residue is taken up in ethyl acetate, washed with sodium bicarbonate and with water, dried with magnesium sulfate, and again concentrated. The residue is triturated with ether and 7β-[[D,L-[[[(4-methoxyphenyl)methoxy]carbonyl]amino]-2-[(chloroacetyl)imino]-2,3-dihydro-4-thiazolyl)acetyl]amino]-3-[(acetyloxy)methyl]-8-oxo-5-thia-1-azabicyclo[4.2.0]oct-2-ene-2-carboxylic acid, diphenylmethyl ester is obtained as a solid residue.

(b)

7β-[[D,L-(2-Amino-2-[(chloroacetyl)imino]-2,3-dihydro-4-thiazolyl)acetyl]amino]-3-[(acetyloxy)methyl]-8-oxo-5-thia-1-azabicyclo[4.2.0]oct-2-ene-2-carboxylic acid, trifluoroacetic acid salt 2 g. of the diphenylmethyl ester product from part (a) are added to a mixture of 30 ml. of trifluoroacetic acid and 6 ml. of anisole at 0°. The mixture is stirred for 10 minutes and the trifluoroacetic acid is then evaporated in vacuo. The residue is treated with ether and the resulting precipitate is filtered under suction to yield 7β-[[D,L-(2-amino-2-[(chloroacetyl]imino]-2,3-dihydro-4-thiazolyl)acetyl]amino]-3-[(acetyloxy)methyl]-8-oxo-5-thia-1-azabicyclo[4.2.0]oct-2-ene-2-carboxylic acid, trifluoroacetic acid salt.

(c)

7β-[[D,L-[(Aminocarbonyl)amino]-(2-[(chloroacetyl)imino]-2,3-dihydro-2,3-dihydro-4-thiazolyl)acetyl]amino]-3-[(acetyloxy)methyl]-8-oxo-5-thia-1-azabicyclo[4.2.0]oct-2-ene-2-carboxylic acid, sodium salt 0.1 mol. of the trifluoroacetic acid salt product from part (b) are suspended in 40 ml. of water. 0.02 mol. of potassium cyanate are added and the mixture is stirred for three hours at room temperature until its appearance is of a slight milky turbidity. This mixture is filtered and the filtrate is adjusted to a pH of 1.5 with 2N hydrochloric acid. The resulting precipitate is filtered under suction to yield 7β-[[D,L-[(aminocarbonyl)amino]-(2-[(chloroacetyl)imino]-2,3-dihydro-4-thiazolyl)acetyl]amino]-3-[(acetyloxy)methyl]-8-oxo-5-thia-1-azabicyclo[4.2.0]oct-2-ene-2-carboxylic acid.

The free acid obtained above is treated with sodium ethylhexanoate according to the procedure of Example 1 (e) to yield the corresponding sodium salt.

EXAMPLE 5

7β-[[D,L-[(Aminocarbonyl)amino]-(2,3-dihydro-2-imino-4-thiazolyl)acetyl]amino]-3-[(acetyloxy)methyl]-8-oxo-5-thia-1-azabicyclo-[4.2.0]oct-2-ene-2-carboxylic acid, sodium salt The 7β-[[D,L-[(aminocarbonyl)amino]-2-[(chloroacetyl)imino]-2,3-dihydro-4-thiazolyl)acetyl]amino]-3-[(acetyloxy)methyl]-8-oxo-5-thia-1-azabicyclo[4.2.0]oct-2-ene-2-carboxylic acid from Example 4 is treated according to the procedure of Example 2 to yield 7β-[[D,L-[(aminocarbonyl)amino]-(2,3-dihydro-2-imino-4-thiazolyl)acetyl]amino]-3-[(acetyloxy)methyl]-8-oxo-5-thia-1-azcbicyclo[4.2.0]oct-2-ene-2-carboxylic acid, sodium salt.

EXAMPLES 6–24

Following the procedure of Examples 1 and 4 but employing the 2-(substituted imino)-2,3-dihydro-α-(protected amino)-4-thiazoleacetic acid shown in Col. I and the 7β-amino cephalosporanic acid ester shown in Col. II one obtains the intermediate shown in Col. III. Removal of the α-amino protecting group and treatment with potassium cyanate yields the product shown in Col. IV. Removal of the imino protecting group according to the procedure of Examples 2 and 5 yields the product shown in Col. V.

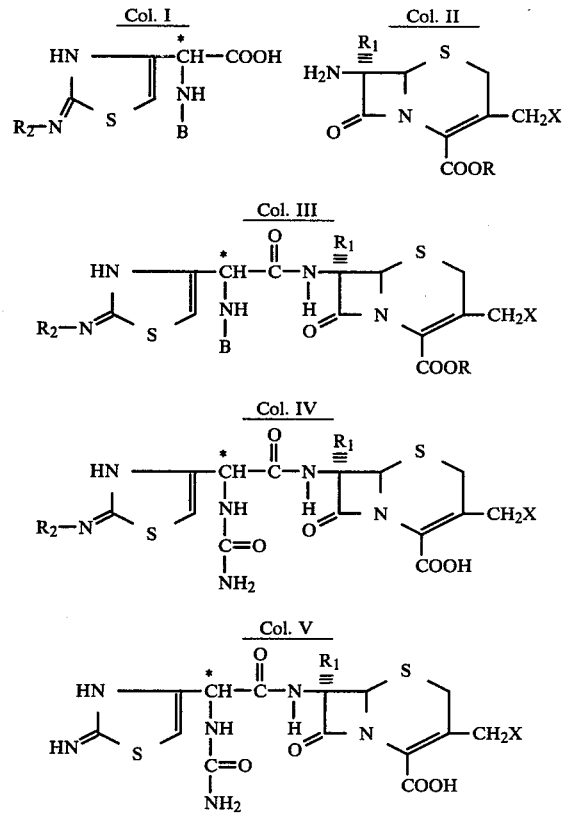

| Example | $R_2$ | B | R | $R_1$ | X |
|---|---|---|---|---|---|
| 6 | —C(O)CH$_2$Cl | —C(O)—O—CH$_2$—C$_6$H$_4$—OCH$_3$ | —CH—(C$_6$H$_5$)$_2$ | —H | —S-triazole-NH |
| 7 | —C(O)CH$_2$Br | —C(O)—O—CH$_2$—C$_6$H$_4$—OCH$_3$ | —CH$_2$—C$_6$H$_5$ | —H | —S-thiadiazole-CH$_3$ |
| 8 | —C(O)—O—CH$_2$CCl$_3$ | —C(O)—O—C(CH$_3$)$_3$ | —CH—(C$_6$H$_5$)$_2$ | —H | —S-triazole-N-C$_2$H$_5$ |

-continued

| Example | R₂ | B | R | R₁ | X |
|---|---|---|---|---|---|
| 9 | —C(=O)—CF₃ | —C(=O)—O—CH₂—C₆H₄—OCH₃ | —CH(—C₆H₅)₂ | —H | —S—C(=N—N=)N(CH₂COOH)— (triazole-thio with CH₂COOH) |
| 10 | —C(=O)—O—CH₂CCl₃ | —C(=O)—O—CH₂—C₆H₄—CH₃ | t-C₄H₉ | —H | —S—C(triazole)N—CH₂—SO₃H |
| 11 | —C(=O)—CH₂Cl | —C(=O)—O—CH₂—C₆H₄—CH₃ | —CH(—C₆H₅)₂ | —H | —S—C(tetrazole)N—(CH₂)₂—N(CH₃)₂ |
| 12 | —CHO | —C(=O)—O—C(CH₃)₃ | —CH₂—C₆H₄—OCH₃ | —H | —O—C(=O)—CH₃ |
| 13 | —C(—C₆H₅)₃ | —C(=O)—O—CH₂—C₆H₄—OCH₃ | —CH(—C₆H₅)₂ | —H | —O—C(=O)—C₂H₅ |
| 14 | —C(—C₆H₅)₃ | —C(=O)—O—CH₂—C₆H₄—OCH₃ | —Si(CH₃)₃ | —H | —H |
| 15 | —C(=O)—CH₂Cl | —C(=O)—O—CH₂—C₆H₄—OCH₃ | —CH₂CCl₃ | —H | —H |
| 16 | —C(=O)—CH₂Cl | —C(=O)—O—CH₂—C₆H₄—OCH₃ | —CH(—C₆H₅)₂ | —H | —O—C(=O)—NH₂ |
| 17 | —C(=O)—O—CH₂CCl₃ | —C(=O)—O—CH₂—C₆H₄—OCH₃ | —CH(—C₆H₅)₂ | —OCH₃ | —O—C(=O)—NH₂ |
| 18 | —C(=O)—CH₂Br | —C(=O)—O—C(CH₃)₃ | —CH₂—C₆H₅ | —OCH₃ | —O—C(=O)—CH₃ |
| 19 | —C(=O)CH₂Cl | —C(=O)—O—CH₂—C₆H₄—OCH₃ | —CH(—C₆H₅)₂ | —OCH₃ | —S—C(thiadiazole, 5-C₂H₅)— |
| 20 | —CHO | —C(=O)—O—CH₂—C₆H₄—OCH₃ | —CH(—C₆H₅)₂ | —OCH₃ | —S—C(tetrazole)N—CH₂—N(C₂H₅)₂ |
| 21 | —C(=O)CH₂Cl | —C(=O)—O—CH₂—C₆H₄—OCH₃ | —CH(—C₆H₅)₂ | —H | —S—C(triazole)N—(CH₂)₂—SO₂OH |

-continued

| Example | R₂ | B | R | R₁ | X |
|---|---|---|---|---|---|
| 22 | −C(=O)CH₂Br | −C(=O)−O−CH₂−C₆H₄−OCH₃ | −CH−(C₆H₅)₂ | −OCH₃ | −S−[1,3,4-thiadiazol-2-yl with N−CH₂COOH] |
| 23 | −C(−C₆H₅)₃ | −C(=O)−O−CH₂−C₆H₄−OCH₃ | −CH−(C₆H₅)₂ | −OCH₃ | −S−[1,3,4-thiadiazol-2-yl with N−CH₃] |
| 24 | −C(=O)−O−CH₂−CCl₃ | −C(=O)−O−CH₂−C₆H₄−OCH₃ | −CH−(C₆H₅)₂ | −H | −S−[1,3,4-thiadiazol-2-yl with N−C₂H₅] |

The cephalosporin acid products of Examples 6 to 24 shown in Col. IV and V can be treated so as to obtain the corresponding sodium or potassium salt. In the case of the compounds of Examples 9, 10, 21 and 22, the disodium or dipotassium salt would be obtained.

Also, the acid products of Examples 6 to 24 shown in Col. IV and V can be treated so as to introduce a different ester group such as the compounds wherein R is

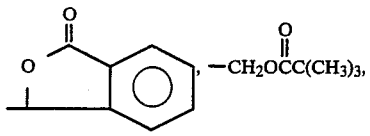
−CH₂OC(=O)C(CH₃)₃, etc.

The compounds of Examples 6 to 24 can be obtained in the D-, L- or D,L-isomeric form.

EXAMPLE 25

7β-[[D,L-[(Aminocarbonyl)amino]-(2,3-dihydro-2-imino-4-thiazolyl)acetyl]amino]-3-[(acetyloxy)methyl]-8-oxo-5-thia-1-azobicyclo[4.2.0]oct-2-ene-2-carboxylic acid, sodium salt The compound of Example 5 can also be prepared according to the following procedure.

(a)

7β-[[D,L-[[[(4-Methoxyphenyl)methoxy]carbonyl]amino]-(2,3-dihydro-2-imino-4-thiazolyl)acetyl]amino]-3-[(acetyloxy)methyl]-8-oxo-5-thia-1-azabicyclo[4.2.0]oct-2-ene-2-carboxylic acid, diphenylmethyl ester 4.38 g. (0.01 mol.) of 7β-amino-3-[(acetyloxy)methyl]-8-oxo-5-thia-1-azabicyclo[4.2.0]oct-2-ene-2-carboxylic acid, diphenylmethyl ester, i.e., 7-ACA diphenylmethyl ester, is dissolved in a mixture of 10 ml. of dimethylformamide and 50 ml. of tetrahydrofuran. A solution of 3.71 g. (0.011 mol.) of D,L-2,3-dihydro-2-imino-α-[[[(4-methoxyphenyl)methoxy]carbonyl]amino]-4-thiazolacetic acid, from Example 1 (a), in 30 ml. of dimethylformamide is added and the resulting mixture is diluted with 200 ml. of tetrahydrofuran. A solution of 2.47 g. of dicyclohexylcarbodiimide in 20 ml. of tetrahydrofuran is added dropwise at 0°–5°. The reaction mixture is stirred for 90 minutes at 0°–5° and then at room temperature. After three hours the mixture is filtered and the filtrate is concentrated in vacuo. The residue is taken up in ethyl acetate, filtered, washed with sodium bicarbonate and water, dried with magnesium sulfate, and concentrated in vacuo. Ether is added to the residue which is then filtered under suction to yield 6.3 g. of 7β-[[D,L-[[[(4-methoxyphenyl)methoxy]carbonyl]amino]-(2,3-dihydro-2-imino-4-thiazolyl)acetyl]amino]-3-[(acetyloxy)methyl]-8-oxo-5-thia-1-azabicyclo[4.2.0]oct-2-ene-2-carboxylic acid, diphenylmethyl ester, m.p. 125°–128°.

(b)

7β-[[D,L-(α-Amino)-(2,3-dihydro-2-imino-4-thiazolyl)acetyl]amino]-3-[(acetyloxy)methyl]-8-oxo-5-thia-1-azabicyclo[4.2.0]oct-2-ene-2-carboxylic acid, trifluoroacetic acid salt (1:2)

6 g. of diphenylmethyl ester product from part (a) is treated with a mixture of 25 ml. of anisole and 60 ml. of trifluoroacetic acid to yield 6.9 g. of crude 7β-[[D,L-(α-amino)-(2,3-dihydro-2-imino-4-thiazolyl)acetyl]amino]-3-[(acetyloxy)methyl]-8-oxo-5-thia-1-azabicyclo[4.2.0]oct-2-ene-2-carboxylic acid, trifluoroacetic acid salt (1:2); m.p. 108°–110° (dec.)

(c)

7β-[[D,L-[(Aminocarbonyl)amino]-(2,3-dihydro-2-imino-4-thiazolyl)acetyl]-3-[(acetyloxy)methyl]-8-oxo-5-thia-1-azabicyclo[4.2.0]oct-2-ene-2-carboxylic acid, sodium salt 6 g. of the crude trifluoroacetic acid salt product from part (b) are added to a solution of 1.8 g. of sodium cyanate in 50 ml. of water. The mixture is stirred for three hours at room temperature and a small amount of insoluble material (0.3 g.) is removed by filtration. The solution is then chromatographed on the ion exchange resin Amberlite XAD-2 and eluted first with water and then with an 80:20 mixture of water and methanol. The fraction containing the desired product is freeze dried to yield 3.65 g. of 7β-[[D,L-[(aminocarbonyl)amino]-(2,3-dihydro-2-imino-4-thiazolyl)acetyl]amino]-3-[[(acetyloxy)methyl]-8-oxo-5-thia-1-azabicyclo[4.2.0]oct-2-ene-2-carboxylic acid, sodium salt; m.p. 157°–160° (dec.).

EXAMPLE 26

7β-[[D-[(Aminocarbonyl)amino]-(2,3-dihydro-2-imino-4-thiazolyl)acetyl]amino]-3-[(acetyloxy)methyl]-8-oxo-5-thia-1-azabicylco[4.2.0]oct-2-ene-2-carboxylic acid, sodium salt and 7β-[[L-[(aminocarbonyl)amino]-(2,3-dihydro-2-imino-4-thiazolyl)acetyl]amino]-3-[(acetyloxy)methyl]-8-oxo-5-thia-1-azabicyclo[4.2.0]oct-2-ene-2-carboxylic acid, sodium salt The D,L-product obtained from Example 25 is separated into the D- and L-isomers by means of preparative high performance liquid chromatography (HPLC) employing a 7 μm reverse phase C-8 column (25 mm ID×250 mm). The eluant employed is a mixture of methanol and 0.01M phosphate buffer (8:92) at a flow rate of 20 ml./min. The separation is performed at room temperature and the eluant is monitored at 254 nm (UV). The L-isomer separates out first followed by the D-isomer. The separated isomers are then treated by HPLC on a 25–40 μm RP-18 column (16 mm ID×250 mm) employing as the solvent a mixture of methanol and water (1:99).

This procedure yields 7β-[[D-[(aminocarbonyl)amino]-(2,3-dihydro-2-imino-4-thiazolyl)acetyl]amino]-3-[(acetyloxy)methyl]-8-oxo-5-thia-1-azabicyclo[4.2.0]oct-2-ene-2-carboxylic acid, sodium salt; NMR (DMSO-$d_6$) δ 2.0 (s), 3.3 (broad s), 4.86 (ABq; J=12.5 Hz), 4.88 (d; J=5 Hz), 5.25 (d; J=8.5 Hz), 5.5 (dd; $J_1$=9 Hz, $J_2$=5 Hz), 5.7 (broad s), 6.38 (s), 6.41 (d; J=8.5 Hz), 6.88 (s), 8.54 (d; J=9 Hz); I.R. (KBr) 1760 cm$^{-1}$; UV$_{max}$ 260 nm., ε=10,319; $[α]_D^{25}$ +30.9 (c=3.3 mg/ml; $H_2O$) and 7β-[[L-[(aminocarbonyl)amino]-[2,3-dihydro-2-imino-4-thiazolyl)acetyl]amino]-3-[(acetyloxy)methyl]-8-oxo-5-thia-1-azabicyclo[4.2.0]oct-2-ene-2-carboxylic acid, sodium salt; NMR (DMSO-$d_6$), δ 2.0 (s), 3.3 (broad s), 4.88 (ABq; J=12.5 Hz), 4.94 (d; J=5 Hz), 5.29 (d; J=8.5 Hz), 5.4 (dd; $J_1$=8.5 Hz, $J_2$=5 Hz), 5.7 (broad s), 6.35 (s), 6.45 (d; J=8.5 Hz), 6.89 (s), 8.64 (d; J=8.5 Hz); I.R. (KBr) 1760 cm$^{-1}$; UV$_{max}$ 258 nm., ε=10,291; $[α]_D^{25}$ +81.8 (c=3.3 mg/ml; $H_2O$).

EXAMPLE 27

7β-[[D,L-[(Aminocarbonyl)amino]-(2,3-dihydro-2-imino-4-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid, sodium salt The compound of Example 2 can also be prepared according to the following procedure.

(a)
7β-[[D,L-[[[(4-Methoxyphenyl)methoxy]carbonyl]amino]-(2,3-dihydro-2-imino-4-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 7β-Amino-3-[[(1-methyl-1H-tetrazol-5-yl)thio]methyl]-8-oxo-5-thia-1-azabicyclo[4.2.0]oct-2-ene-2-carboxylic acid, diphenylmethyl ester is reacted with D,L-2,3-dihydro-2-imino-α-[[[(4-methoxyphenyl)methoxy]carbonyl]amino]-4-thiazoleacetic acid according to the procedure of Example 25 (a) to yield 7β-[[D,L-[[[(4-methoxyphenyl)methoxy]carbonyl]amino]-(2,3-dihydro-2-imino-4-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester.

(b) 7β-[[D,L-(α-Amino)-(2,3-dihydro-2-imino-4-thiazolyl)acetyl]amino]-3-[[(1-methyl-1H-tetrazol-5-yl)thio]methyl]-8-oxo-5-thia-1-azabicyclo[4.2.0]-oct-2-ene-2-carboxylic acid, trifluoroacetic acid salt The diphenylmethyl ester from part (a) is treated with a mixture of trifluoroacetic acid and anisole according to the procedure of Example 25 (b) to yield 7β-[[D,L-(α-amino)-(2,3-dihydro-2-imino-4-thiazolyl)acetyl]amino]-3-[[(1-methyl-1H-tetrazol-5-thia-1-azabicyclo[4.2.0]oct-2-ene-2-carboxylic acid, trifluoroacetic acid salt.

(c)
7β-[[D,L-[(Aminocarbonyl)amino]-(2,3-dihydro-2-imino-4-thiazolyl)acetyl]amino]-3-[[(1-methyl-1H-tetrazol-5-yl)thio]methyl]-8-oxo-5-thia-1-azabicyclo-[4.2.0]oct-2-ene-2-carboxylic acid, sodium salt The trifluoroacetic acid salt product from part (b) is treated with sodium cyanate to yield 7β-[[D,L-[(aminocarbonyl)amino]-(2,3-dihydro-2-imino-4-thiazolyl)acetyl]amino]-3-[[(1-methyl-1H-tetrazol-5-yl)thio]methyl]-8-oxo-5-thia-1-azabicyclo-[4.2.0]oct-2-ene-2-carboxylic acid.

This acid is then treated with sodium ethylhexanoate as taught in Example 1(e) to yield the corresponding sodium salt.

EXAMPLES 28–39

Following the procedure of Example 25 but employing the 2,3-dihydro-2-imino-α-protected amino-4-thiazoleacetic acid shown in Col. I and the 7β-amino cephalosporanic acid ester shown in Col. II one obtains the intermediate shown in Col. III. The α-amino protecting group and the ester protecting group are then removed and the intermediate is reacted with sodium cyanate and treated to obtain the sodium salt shown in Col. IV.

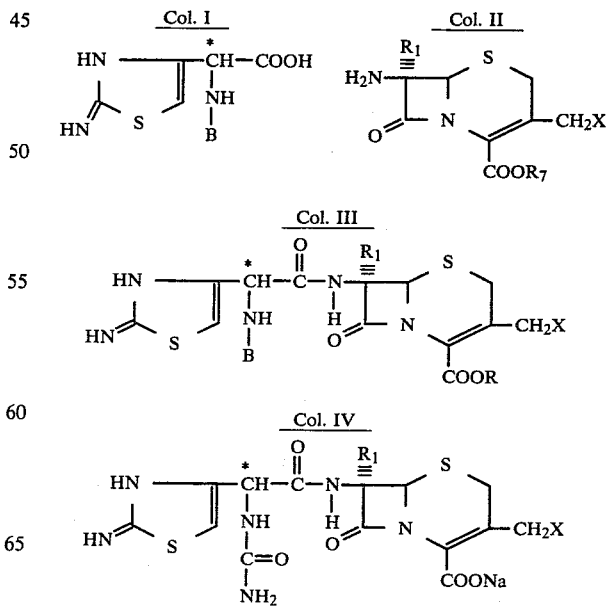

| Example | R$_1$ | X | R$_7$ | B |
|---|---|---|---|---|
| 28 | —H | -S-C(=N-N=N-N(C$_2$H$_5$))- (1-ethyl-tetrazol-5-yl-thio) | —CH(—C$_6$H$_4$—)$_2$ | —COCH$_2$—C$_6$H$_4$—OCH$_3$ |
| 29 | —H | -S-C(=N-N=N-N((CH$_2$)$_2$N(CH$_3$)$_2$))- | —CH(—C$_6$H$_4$—)$_2$ | —COCH$_2$—C$_6$H$_4$—OCH$_3$ |
| 30 | —H | -S-C(=N-N=N-N(CH$_2$COONa))- | —CH(—C$_6$H$_4$—)$_2$ | —COCH$_2$—C$_6$H$_4$—OCH$_3$ |
| 31 | —H | -S-C(=N-N=N-N(CH$_2$SO$_3$Na))- | —CH(—C$_6$H$_4$—)$_2$ | —COCH$_2$—C$_6$H$_4$—OCH$_3$ |
| 32 | —H | -S-C(=N-N=C(CH$_3$)-S)- (5-methyl-1,3,4-thiadiazol-2-yl-thio) | —CH(—C$_6$H$_4$—)$_2$ | —COCH$_2$—C$_6$H$_4$—OCH$_3$ |
| 33 | —H | —H | —CH(—C$_6$H$_4$—)$_2$ | —COCH$_2$—C$_6$H$_4$—OCH$_3$ |
| 34 | —H | —OC(=O)NH$_2$ | —CH(—C$_6$H$_4$—)$_2$ | —COCH$_2$—C$_6$H$_4$—OCH$_3$ |
| 35 | —OCH$_3$ | -S-C(=N-N=N-N(CH$_3$))- | —CH(—C$_6$H$_4$—)$_2$ | —COCH$_2$—C$_6$H$_4$—OCH$_3$ |
| 36 | —OCH$_3$ | -S-C(=N-N=N-N((CH$_2$)$_2$N(CH$_3$)$_2$))- | —CH(—C$_6$H$_4$—)$_2$ | —COCH$_2$—C$_6$H$_4$—OCH$_3$ |
| 37 | —OCH$_3$ | —OC(=O)CH$_3$ | —CH(—C$_6$H$_4$—)$_2$ | —COCH$_2$—C$_6$H$_4$—OCH$_3$ |
| 38 | —H | —OC(=O)CH$_3$ | —CH$_2$—C$_6$H$_5$ | —C(=O)—O—C(CH$_3$)$_3$ |

-continued

| Example | R₁ | X | R₇ | B |
|---------|----|----|-----|---|
| 39 | —H | 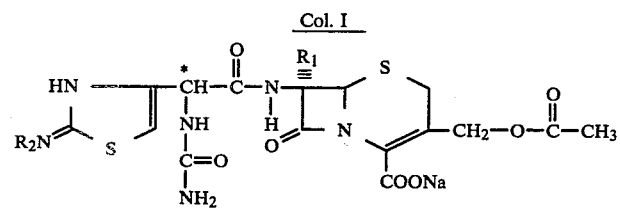 |  | 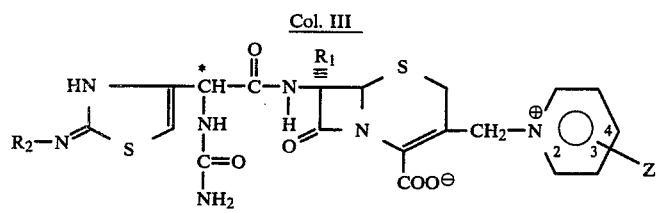 |

The compounds of Examples 28 to 39 can be obtained in the D-, L-, or D,L-isomer form.

EXAMPLE 40

7β-[[D,L-[(Aminocarbonyl)amino]-(2,3-dihydro-2-imino-4-thiazolyl)acetyl]amino-3-[[4-(aminocarbonyl)-pyridino]methyl]-8-oxo-5-thia-1-azabicyclo[4.2.0]-oct-2-ene-2-carboxylic acid A mixture of 0.005 mole of the sodium salt product of Example 25, 0.0075 mole of 4-pyridinecarboxamide, 12 g. of potassium thiocyanate, and 7.5 ml. of water are heated at 50° for 24 hours. The resulting solution is passed through a chromatography column filled with 150 g. of ion exchanger Amberlite XAD-2. The column is washed with about 3 liters of water and the titled compound is eluted with a mixture of water:methanol (8:2). The methanol is evaporated from the eluate and the aqueous solution is lyophilized. The amorphous residue is triturated with ether and filtered under suction to yield 7β-[[D,L-[(aminocarbonyl)amino]-(2,3-dihydro-2-imino-4-thiazolyl)acetyl]amino-3-[[4-(aminocarbonyl)pyridino]methyl]-8-oxo-5-thia-1-azabicyclo[4.2.0]oct-2-ene-2-carboxylic acid.

In a similar manner by employing the sodium salt product of Example 4 in the above procedure one obtains, 7β-[[D,L-[(aminocarbonyl)amino]-(2-[(chloroacetyl)imino]-2,3-dihydro-4-thiazolyl)acetyl]-amino]-3-[[4-(aminocarbonyl)pyridino]methyl]-8-oxo-5-thia-1-azabicyclo[4.2.0]oct-2-ene-2-carboxylic acid.

EXAMPLES 41–57

Following the procedure of Example 40 but employing the cephalosporanic acid sodium salt shown in Col. I and the pyridine compound shown in Col. II, one obtains the product shown in Col. III.

Col. I

Col. II

Col. III

| Example | R₂ | R₁ | Z |
|---------|----|----|----|
| 41 | —H | —H | —H |
| 42 | —H | —H | —CNH₂ (3) (O) |
| 43 | —H | —OCH₃ | —H |
| 44 | —H | —OCH₃ | —CNH₂ (4) (O) |
| 45 | —CCH₂Cl (O) | —OCH₃ | —CNH₂ (4) (O) |
| 46 | —CCH₂Cl (O) | —H | —H |
| 47 | —CCH₂Br (O) | —OCH₃ | —H |
| 48 | —C—O—CH₂CCl₃ (O) | —H | —CNH₂ (2) (O) |
| 49 | —C—O—CH₂CCl₃ (O) | —H | —CNH₂ (4) (O) |
| 50 | —C—CF₃ (O) | —H | —H |

-continued

| Example | R₂ | R₁ | Z |
|---|---|---|---|
| 51 | −C(=O)−CF₃ | −H | −CNH₂ (4) (C=O) |
| 52 | −C(=O)−CF₃ | −OCH₃ | −H |
| 53 | −CH(=O) | −H | −H |
| 54 | −CH(=O) | −OCH₃ | −CNH₂ (4) (C=O) |
| 55 | 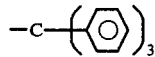 | −H | −H |
| 56 | −C−(C₆H₅)₃ | −H | −CNH₂ (4) (C=O) |
| 57 | −C−(C₆H₅)₃ | OCH₃ | −CNH₂ (4) (C=O) |

The final products of Examples 41–57 are obtained in the D—, L—, or D,L—isomeric form depending upon the isomeric form of the cephalosporin shown in Col. I.

EXAMPLE 58

7β-[[D,L-[(Aminocarbonyl)amino]-(2,3-dihydro-2-
-imino-4-thiazolyl)acetyl]amino]-3-[[(2-methyl-1,3,4-
thiadiazol-5-yl)thio]methyl]-[-oxo-5-thia-1-azabicyclo-
[4.2.0]oct-3-ene-2-carboxylic acid, sodium salt 0.002 mol. of the sodium salt product of Example 25 is brought into solution in 100 ml. of a phosphate buffer at a pH of 6.4. Then 0.0024 mol. of 5-methyl-1,3,4-thiadiazolyl-2-thiol is added. The solution is heated at 60° for six hours. After cooling, the pH is adjusted to 7.0 and the solution is chromatographed on the ion exchange resin Amberlite XAD-2. The fraction containing the desired product is freeze dried to yield 7β-[[D,L-[(aminocarbonyl)amino]-(2,3-dihydro-2-imino-4-thiazolyl)acetyl]amino]-3-[[(2-methyl-1,3,4-thiadiazol-5-yl)thio]methyl]-8-oxo-5-thia-1-azabicyclo[4.2.0]oct-2-ene-2-carboxylic acid, sodium salt.

In a similar manner by employing the sodium salt product of Example 4 in the above procedure one obtains, 7β-[[D,L-[(aminocarbonyl)amino]-(2-[(chloro acetyl)imino]-2,3-dihydro-4-thiazolyl)acetyl]amino]-3-[[(2-methyl-1,3,4-thiadiazol-5-yl)thio]methyl]-8-oxo-5-thia-1-azabicyclo[4.2.0]oct-2-ene-2-carboxylic acid, sodium salt.

EXAMPLES 59–69

Following the procedure of Example 58 but employing the cephalosporanic acid sodium salt shown in Col. I and the thiol shown in Col. II, one obtains the product shown in Col. III.

Col. I

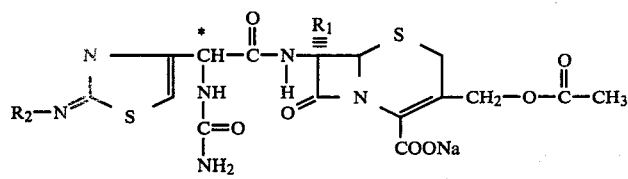

Col. II

HS—hetero

Col. III

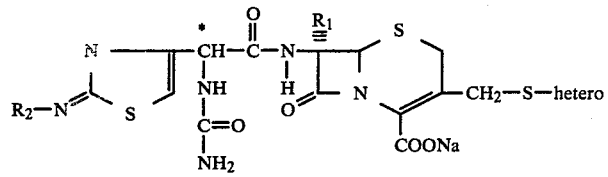

| Example | R₁ | R₂ | hetero |
|---|---|---|---|
| 59 | −OCH₃ | −CCH₂Cl (C=O) | N—N, S, CH₃ (thiadiazole) |
| 60 | −H | −H | N—N, S, CH₃ (thiadiazole) |
| 61 | −H | −CCH₂Br (C=O) | N—N, N−N−CH₃ (tetrazole, N-methyl) |
| 62 | −OCH₃ | −H | N—N, N−N−C₂H₅ (tetrazole, N-ethyl) |
| 63 | −H | −C−O−CH₂CCl₃ (C=O) | N—N, N−N−CH₂COONa (tetrazole) |

| Example | R₁ | R₂ | hetero |
|---|---|---|---|
| 64 | —OCH₃ | —C—(phenyl)₃ | 1-methyl-tetrazolyl-S with CH₂—S(=O)₂—ONa substituent |
| 65 | —H | —C—(phenyl)₃ | same tetrazole with CH₂—S(=O)₂—ONa |
| 66 | —H | —H | tetrazole with (CH₂)₂N(CH₃)₂ |
| 67 | —H | —C(=O)—CF₃ | tetrazole with CH₃ |

The final products of Examples 59–69 are obtained in the D—, L— or D,L—isomeric form depending upon the isomeric form of the cephalosporin shown in Col. I.

What is claimed is:

1. A compound of the formula

[structure: cephalosporin with HN—C(=NR₂)—S ring, CH—C(=O)—N(R₁)— linked to β-lactam, NH—C(=O)—NH₂ side chain, CH₂X at 3-position, COOR at 2-position]

including its amino tautomer form wherein R is hydrogen, sodium, potassium, —CH₂—O—lower alkyl, $$-\underset{R_3}{\underset{|}{CH}}-O-\overset{O}{\underset{\|}{C}}-\text{lower alkyl, or } -O-\overset{O}{\underset{\|}{C}}-\text{phenyl};$$

R₁ is in the α-configuration and is hydrogen or methoxy; R₂ is hydrogen, $$-\overset{O}{\underset{\|}{C}}CH_2Cl, -\overset{O}{\underset{\|}{C}}CH_2Br, -\overset{O}{\underset{\|}{C}}-CF_3, -\overset{O}{\underset{\|}{C}}-O-CH_2CCl_3,$$

$$-\overset{O}{\underset{\|}{C}}H \text{ or } -C-(\text{phenyl})_3;$$

R₃ is hydrogen or lower alkyl; X is $$-S-\underset{S}{\overset{N=N}{\underset{\|}{\diagdown}}}-R_4, \text{ or } -S-\underset{\underset{R_5}{|}}{\overset{N=N}{\underset{N}{\diagdown}}}-N;$$

R₄ is hydrogen of lower alkyl; R₅ is hydrogen, lower alkyl, $$-(CH_2)_n-\overset{O}{\underset{\|}{C}}-OR_6, -(CH_2)_n-\overset{O}{\underset{\|}{S}}-OR_6,$$
$$\phantom{-(CH_2)_n-}\underset{O}{\|}$$

or —(CH₂)ₙ—N—(lower alkyl)₂;

R₆ is hydrogen, sodium or potassium; and n is an integer from 1 to 4.

2. The compound of claim 1 wherein R is hydrogen, sodium, or potassium; R₁ is hydrogen; R₂ is hydrogen or $$-\overset{O}{\underset{\|}{C}}CH_2Cl; X \text{ is } -S-\underset{S}{\overset{N=N}{\underset{\|}{\diagdown}}}-CH_3, \text{ or } -S-\underset{\underset{R_5}{|}}{\overset{N=N}{\underset{N}{\diagdown}}}-N;$$

R₅ is hydrogen, methyl, $$-CH_2-\overset{O}{\underset{\|}{C}}-OR_6, -CH_2-\overset{O}{\underset{\|}{S}}-OR_6,$$
$$\phantom{-CH_2-}\underset{O}{\|}$$

or —(CH₂)₂N(CH₃)₂; and R₆ is hydrogen, sodium or potassium.

3. The compound of claim 2 wherein R₂ is hydrogen.

4. The compound of claim 3 wherein X is $$-S-\underset{\underset{CH_3}{|}}{\overset{N=N}{\underset{N}{\diagdown}}}-N.$$

5. The compound of claim 4, 7β-[[D,L-[(aminocarbonyl)amino-(2,3-dihydro-2-imino-4-thiazolyl)acetyl]-amino]-3-[[(1-methyl-1H-tetrazol-5-yl)thio]methyl]-8-oxo-5-thia-1-azabicyclo[4.2.0]oct-2-ene-2-carboxylic acid.

6. The sodium salt of the compound of claim 5.

7. The compound of claim 4, 7β-[[D-[(aminocarbonyl)amino]-(2,3-dihydro-2-imino-4-thiazolyl)acetyl]amino]-3-[[(1-methyl-1H-tetrazole-5-yl)thio]methyl]-8-oxo-5-thia-1-azabicyclo[4.2.0]oct-2-ene-2-carboxylic acid.

8. The sodium salt of the compound of claim 7.

9. The compound of claim 4, 7β-[[L-[(aminocarbonyl)amino]-(2,3-dihydro-2-imino-4-thiazolyl)acetyl]amino]-3-[[(1-methyl-1H-tetrazol-5-yl)thio]methyl]-8-oxo-5-thia-1-azabicyclo[4.2.0]oct-2-ene-2-carboxylic acid.

10. The sodium salt of the compound of claim 9.

11. The compound of claim 3 wherein X is

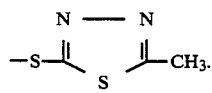

12. The compound of claim 3 wherein X is

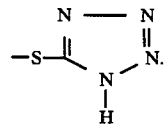

13. The compound of claim 3 wherein X is

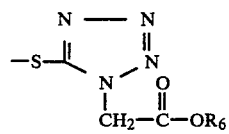

and $R_6$ is hydrogen, sodium or potassium.

14. The compounds of claim 3 wherein X is

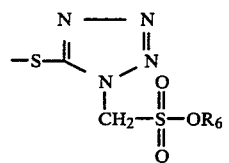

and $R_6$ is hydrogen, sodium or potassium.

15. The compound of claim 3 wherein X is

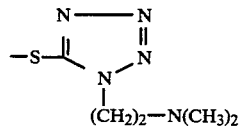

16. The compound of claim 2 wherein $R_2$ is

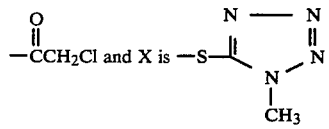

17. A compound of the formula

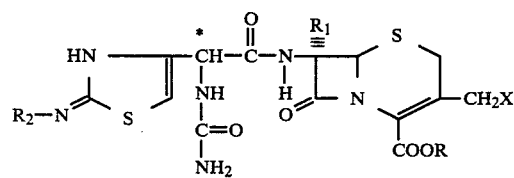

including its amino tautomer form wherein R is t-butyl, benzyl; p-methoxybenzyl, p-nitrobenzyl, diphenylmethyl, 2,2,2-trichloroethyl or trimethylsilyl; $R_1$ is in the α-configuration and is hydrogen or methoxy; $R_2$ is hydrogen,

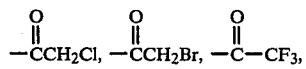

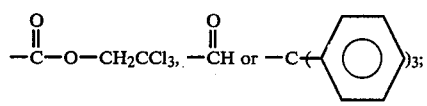

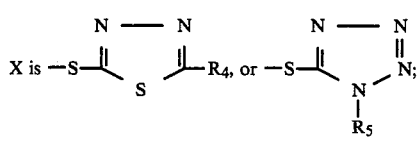

$R_4$ is hydrogen or lower alkyl;
$R_5$ is hydrogen, lower alkyl,

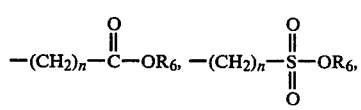

or $-(CH_2)_n-N-(\text{lower alkyl})_2$;
$R_6$ is hydrogen, sodium or potassium; and n is an integer from 1 to 4.

18. An antibacterial pharmaceutical composition comprising a pharmaceutically acceptable carrier and one or more antibacterially active compounds of the formula

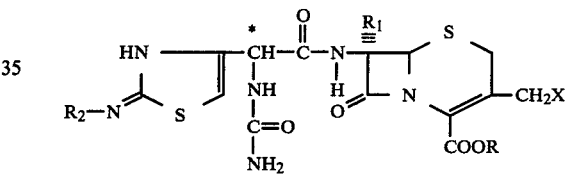

wherein R is hydrogen, sodium, potassium, —$C_2$—O—lower alkyl,

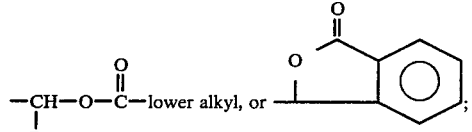

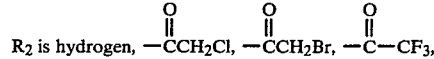

$R_1$ is in the α-configuration and is hydrogen or methoxy; $R_3$ is hydrogen or lower alkyl; X is

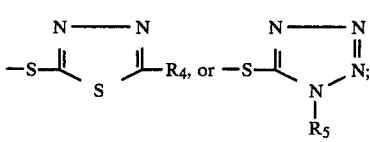

$R_4$ is hydrogen or lower alkyl;
$R_5$ is hydrogen, lower alkyl,

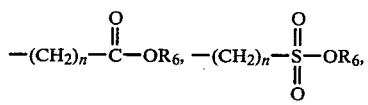

or —$(CH_2)_n N(lower\ alkyl)_2$; $R_6$ is hydrogen, sodium or potassium; and n is an integer from 1 to 4.

19. The composition of claim 18 wherein R is hydrogen, sodium, or potassium; $R_1$ is hydrogen; X is

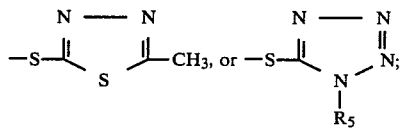

$R_5$ is hydrogen, methyl,

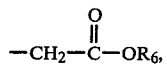

—$CH_2$—$SO_3R_6$, or —$(CH_2)_2$-$N(CH_3)_2$; and $R_6$ is hydrogen, sodium or potassium.

20. The composition of claim 19 wherein X is

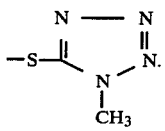

21. The method of treating a bacterial infection in a mammal which comprises parenterally administering an antibacterially effective amount of the composition of claim 18.

22. The compound 7-[2-(2-aminothiazol-4-yl)-2-(aminocarbonylamino)acetamido]-3-(1-methyl-1H-tetrazol-5-yl)thiomethyl-3-cephem-4-carboxylic acid or the sodium carboxylate thereof.

* * * * *